United States Patent [19]

Herauf

[11] Patent Number: 5,080,972

[45] Date of Patent: Jan. 14, 1992

[54] PARTICULATE MONITORING TAPE

[75] Inventor: Leroy J. Herauf, Austin, Tex.

[73] Assignee: Minnesota Mining and Manufacturing Company, St. Paul, Minn.

[21] Appl. No.: 400,668

[22] Filed: Aug. 30, 1989

[51] Int. Cl.$^5$ .......................... B32B 7/12; B32B 15/04
[52] U.S. Cl. ..................................... 428/343; 428/40; 428/195; 428/207
[58] Field of Search .......................... 428/40, 343, 354

[56] References Cited

U.S. PATENT DOCUMENTS

| | | | |
|---|---|---|---|
| 3,203,870 | 8/1965 | Andelin | 195/139 |
| 3,684,660 | 8/1972 | Kereluk et al. | 195/139 |
| 4,237,223 | 12/1980 | Metz | 428/343 X |
| 4,465,729 | 8/1984 | Cancio et al. | 428/343 X |
| 4,713,274 | 12/1987 | Minor | 428/40 |
| 4,895,745 | 1/1990 | Vesley et al. | 428/343 X |

FOREIGN PATENT DOCUMENTS 47-6040  2/1972  Japan .

OTHER PUBLICATIONS

ASTM Standard No. F24-65 (reapproved 1983). Operating and Maintenance Instructions—(revision data of Jan. 1982).
*Handbook on Aerosols* (edited by R. Dennis, 1976), pp. 95-96.
*Air Pollution* (edited by A. Stern, 1968), vol. II, pp. 250-251.
*Methods of Air Sampling and Analysis* (edited by M. Katz, latest copyright 1977), pp. 585-587 and 624-629.

*Primary Examiner*—George F. Lesmes
*Assistant Examiner*—D. R. Zirker
*Attorney, Agent, or Firm*—Gary L. Griswold; Walter N. Kirn; Jack V. Musgrove

[57] ABSTRACT

A tape for sampling a surface to determine the amount of particulate matter which has settled thereon. The tape is constructed of a polymeric film backing and a smooth, pigmented adhesive coating. A grid pattern is printed directly on the outer surface of the adhesive coating. In this manner, the tape may be applied directly to the surface to be sampled, and particulates will adhere to the outer surface of the adhesive coating. The particulate level may then be determined according to the average number of particulates in a given square formed by the grid pattern.

10 Claims, 1 Drawing Sheet

PARTICULATE MONITORING TAPE

BACKGROUND OF THE INVENTION

1. Field of the Invention

The present invention generally relates to articles and devices for measuring the amount of particulates which have settled on a surface, and more particularly to an adhesive, gridded tape used to collect and analyze such particulates.

2. Description of the Prior Art

There are two primary applications of monitoring the air for particulate levels and distributions, namely, outdoor air pollution studies and indoor quality control. The Environmental Protection Agency (as well as its counterparts in other countries) has established maximum ambient levels for particulates of different sizes to insure the health and safety of individuals. The EPA usually requires impact studies before issuing a permit to build a facility which would introduce additional particulate pollutants into the atmosphere. Such studies include measurement of present particulate levels and projections of future levels after the planned facility is built and in operation.

Particulate control is also important in indoor applications, such as graphic arts houses and medical laboratories, and even more crucial in "clean rooms." Clean rooms are necessary for the fabrication of sensitive semiconductor components such as integrated circuits which are extremely susceptible to contamination by airborne dust and fibrils. Companies have gone to great lengths to minimize the presence of these fine particles, including the use of room air ionizers and filtration systems, but it is still necessary to monitor ambient particulate levels to insure proper quality control in the manufacture of the electronic components. Clean rooms are also used in non-electronic manufacturing facilities, such as in the manufacture of magnetic recording media.

There are two principle methods for sampling particulate pollutants, viz., filtration and gravimetric settlement. Filtration techniques usually require that a surface or object be washed with a liquid solvent, and the effluent collected and filtered (see ASTM test procedure F24-83). This procedure, however, has several drawbacks, such as the fact that fibrous filters are unsuitable for collecting fine particles as they tend to penetrate into the body of the filtering medium. Molecular or membrane filters can be used, but they are more expensive and necessitate the use of additional accessories. An example of a filtration device designed for measuring particulate contamination is the unit sold by Millipore Corp. of Bedford, Mass., under model number XX1004730.

The second method for sampling is by gravity or settlement, i.e., allowing particles suspended in the air to descend onto fallout jars, plates, glass slides, etc. Microscopic techniques may then be used to count the number of particles per specified area. In the past, this technique has also been employed using adhesive-coated paper. For example, an established method for analyzing the amount of wind-blown particles as a function of wind direction requires that an adhesive strip be annularly mounted on the surface of a cylindrical holder.

Settlement techniques are, nonetheless, still crude with respect to determination of the amount of particles per unit area. One rudimentary solution is to cut the strip into squares of unit area (e.g., one square inch), and then count the number of particulates on each square, arriving at an average value. The introduction of the cutting step, however, provides room for further human error. An alternative method requires the use of a complicated device known as a Gruber Comparator, in which photographic standards are compared to the collected sample. Use of such a device is undesirable inasmuch as 1) it involves extra expense, 2) it requires previous calibration of the photographic standards, and 3) it requires a subjective comparison of visual images. It would, therefore, be desirable and advantageous to devise an article which would simplify the collection and measurement of suspended particulates.

Accordingly, the primary object of the present invention is to provide an article for monitoring ambient particulate levels.

Another object of the invention is to provide such an article which may easily be used without any special training.

Still another object of the invention is to provide a particulate collection device which simplifies determination of the number of particulates in a given area.

SUMMARY OF THE INVENTION

The foregoing objects are achieved in a particulate monitoring tape having a dimensionally stable polymeric film backing, a pigmented adhesive coated on the film, and a fine lined grid pattern printed on the surface of the adhesive. In the preferred embodiment, the adhesive is white and the printing black, with grid sizes of 3.16 mm×3.16 mm. The particulate monitoring tape is manufactured in clean room conditions, and packaged in a sealed dispenser.

BRIEF DESCRIPTION OF THE DRAWINGS

The novel features of the invention are set forth in the appended claims. The invention itself, however, will best be understood by reference to the accompanying drawings, wherein:

DESCRIPTION OF THE PREFERRED EMBODIMENT

Figure 1:
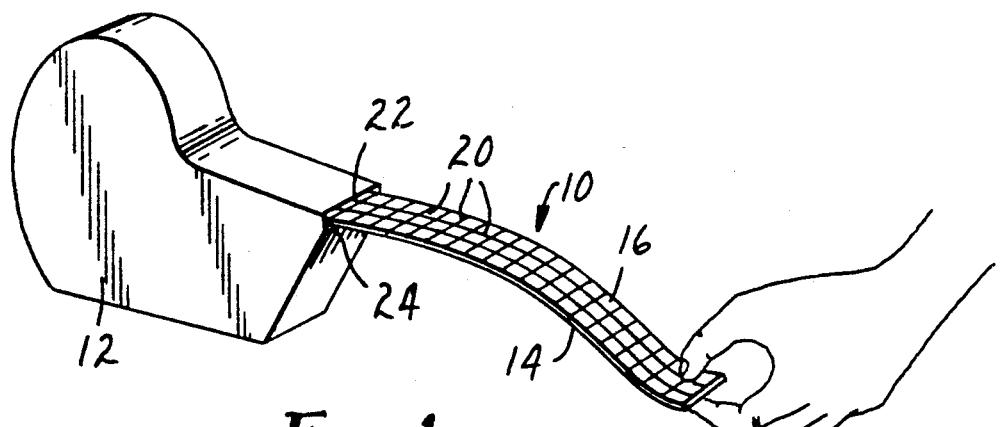
FIG. 1 is a perspective view showing the particulate monitoring tape of the present invention as packaged in the clean dispenser.
Figure 2:
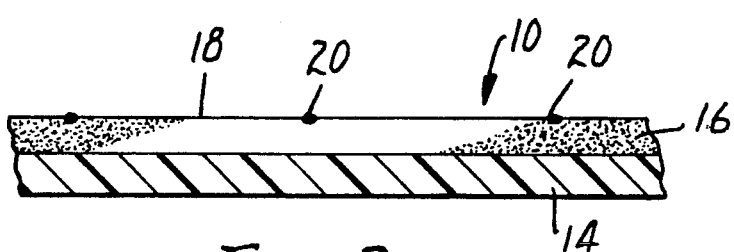
FIG. 2 is an enlarged cross-sectional view of the particulate monitoring tape showing its layered construction.

With reference now to the figures, and in particular with reference to FIGS. 1 and 2, there is depicted the particulate monitoring tape 10 of the present invention, along with a sealed dispenser 12. In the preferred embodiment, particulate monitoring tape 10 includes two layers, a film backing 14 and a pressure-sensitive adhesive coating 16. Film backing 14 may be constructed of any durable material, and is preferably formed from a polymeric sheet, such as polyester, which is dimensionally stable and highly resistant to solvents. The thickness of polyester film 14 may vary considerably, but is optimally about 1.0 mil (25 micrometers). In this regard, it is understood that the cross-section of FIG. 2 is not necessarily to scale due to the extremely small thicknesses involved.

Adhesive coating 16 is opaque, i.e., pigmented so as to provide a high contrast with the particulates during the counting procedure. Adhesive coating 16 typically has a thickness of about 1.0 mil (25 micrometers). The adhesive used in forming coating 16 should be smooth in order to make proper contact with the surface to be sampled. Likewise, film backing 14 should be smooth to insure that the outer surface 18 of adhesive coating 16 is smooth. Also, the adhesion level is preferably not higher than about 25 oz./in., which is sufficient to pick up particulates which would be released under standard conditions. An overly tacky adhesive might remove particulates which normally would not be a problem. Finally, the adhesive should be long aging and firm to avoid leaving a residue on the sampled surface. Acrylic adhesives have been found acceptable. A tape which meets these general requirements for film backing 14 and adhesive coating 16 is sold by Minnesota Mining & Manufacturing Co. (assignee of the present invention) under catalog number 850.

Particulate monitoring tape 10 has a grid pattern impressed thereon. The pattern is printed directly on outer surface 18 of adhesive coating 16, and is composed of a plurality of orthogonal lines 20. In this manner, the grid lies on the same plane as the particulates being counted, which reduces errors due to parallax, and becomes increasingly important with smaller particle size. A buried grid pattern could be utilized wherein the grid is printed on the film backing, and the adhesive is transparent (non-pigmented). This is deemed inferior, however, since it creates a parallax which may result in counting errors, it does not provide the contrast of a pigmented adhesive, and it would require that the adhesive be clean and defect free.

The width of lines 20 should be very small to facilitate counting, a width of about 4 mils (0.1 mm) being preferred. It is anticipated that the pigmented adhesive coating 16 would be white, so lines 20 should be black for easy delineation. If, however, tape 10 is to be used in an area where airborne particles are likely to be of a lighter color, then coating 16 should incorporate a black pigment and lines 20 would be white. The pattern is preferably printed using flexographic techniques (aniline printing), although other processes may be used. See, e.g., Japanese Patent (Kokoku) No. 47-6040, assigned to Sekisui Chemical Co.

The process of manufacture is similar to prior art processes for making tape. A polymeric sheet is coated with the pigmented adhesive, the grid printed thereon, and the sheet spirally wound into a roll. The roll may then be cut axially to produce narrow strips. Particulate monitoring tape 10 is itself ideally manufactured in a clean room environment, so as to minimize the number of particles adhering to the surface 18 of adhesive coating 16. Whether or not a clean room is so used, a background check of the ambient particulates in the manufacturing area should be made. Alternatively, the user may check the background particulate level just prior to use. This background level may then be subtracted from any sampled values. Tape 10 is advantageously packaged in a sealed dispenser 12 which prevents premature exposure of tape lo to airborne contaminants. Dispenser 12 is similar to prior art tape dispensers but dispenser 12 is completely sealed except for a small slot 22 through which tape 10 exits. Slot 22 may be provided with an adjacent cutting blade or straightedge 24 to assist in detaching a piece of tape 10 from the roll remaining in dispenser 12.

Figure 3:
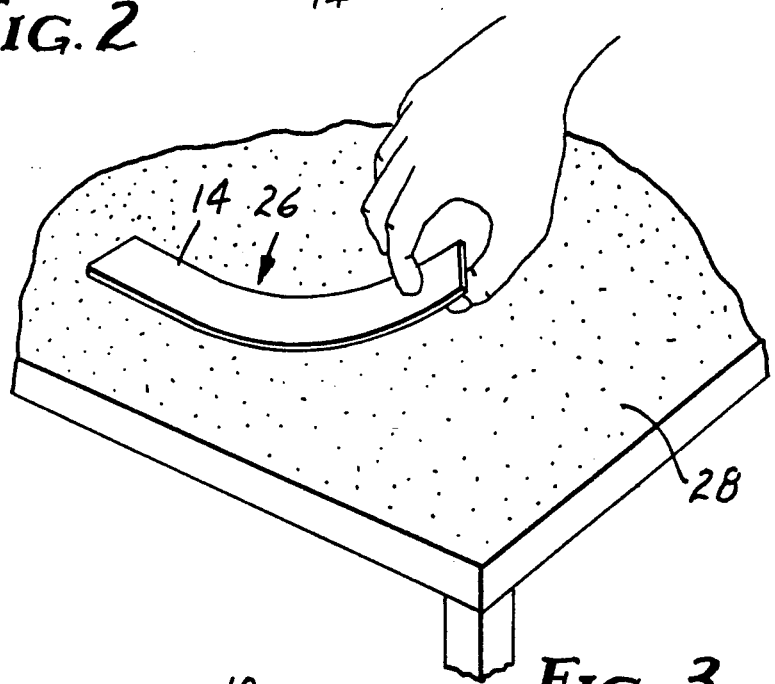
FIG. 3 is a perspective view illustrating use of the particulate monitoring tape on a contaminated surface.
Figure 4:
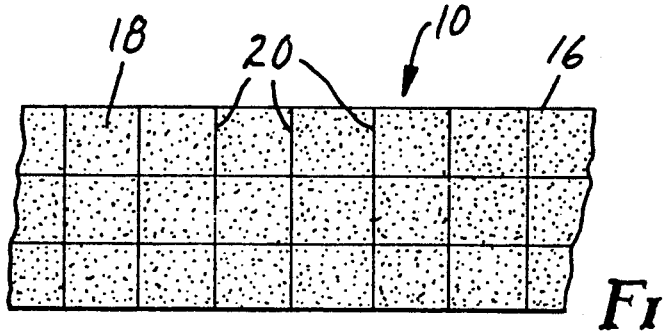
FIG. 4 is a top plan view of the particulate monitoring tape after use.

Referring now to FIGS. 3 and 4, use of particulate monitoring tape 10 is explained. After a strip 26 of tape 10 has been removed from dispenser 12, it is placed on a surface 28 to be sampled, with adhesive coating 16 facing down, i.e., with surface 18 of adhesive coating 16 in contact with surface 28. Strip 26 is pressed lightly against surface 28, and then peeled away. The flexible nature of tape 10 allows use thereof on either smooth or irregular surfaces. After sampling surface 28, strip 26 may be placed under a low power microscope for viewing and counting of the number of particulates. A legend or reference scale (not shown) may optionally be printed at intervals along surface 18 of adhesive coating 16 to facilitate determination of particle size.

The spacing between grid lines 20 may vary, but in order to expedite the sampling method, lines 20 should be spaced so as to form squares having simplified dimensions. For example, if the sampling is expected to yield particulates smaller in size than about 50 microns, then the squares formed by lines 20 are preferably 3.16 millimeters on a side, yielding an area of 10 square mm. Ten such squares may be sampled, the results summed and multiplied by 10,000 to immediately give a value in particulates per square meter. If particulates greater than about 50 microns are expected, then a larger grid size may be used, e.g., one centimeter on a side, yielding an area of one square centimeter. Ten such squares might be sampled, summed and multiplied by 1,000, again yielding a value in particulates per square meter. Particles lying directly over a line may or may not be counted. It is suggested that any particles lying on two of the four lines in a given square (e.g., the top line and the left line) be included in a count. Of course, other grid shapes besides squares may be used, e.g., rectangles.

Although the invention has been described with reference to specific embodiments, this description is not meant to be construed in a limiting sense. Various modifications of the disclosed embodiment, as well as alternative embodiments of the invention, will become apparent to persons skilled in the art upon reference to the description of the invention. For example, the bottom surface of film backing 14 could be provided with another adhesive layer whereby the tape could be affixed to the surface to be monitored, allowing dust to settle directly onto tape 10. It is therefore contemplated that the appended claims will cover such modifications that fall within the true scope of the invention.

I claim:

1. An article for sampling particulates on a surface, comprising:

a durable film backing fabricated from a sheet of dimensionally stable polymeric material;

an adhesive coating affixed to said film backing, said adhesive coating having an outer surface, and having a grid pattern on said outer surface, for visually dividing said adhesive coating into areas of predetermined size; and said adhesive coating being pigmented to provide a contrast with said grid pattern.

2. The article of claim 1 wherein said grid pattern includes a plurality of orthogonal lines having a width of about 0.1 millimeters.

3. The article of claim 1 wherein said adhesive coating is fabricated from a pressure sensitive adhesive having an adhesion of not more than about 25 oz./in.

4. The article of claim 1 wherein said adhesive coating includes a white pigment, and said grid pattern is in black ink.

5. The article of claim 1 wherein said film backing means is fabricated from a sheet of dimensionally stable polymeric material.

6. The article of claim 4 wherein said pressure sensitive adhesive is an acrylic adhesive.

7. The article of claim 1 wherein said polymeric material is polyester.

8. A tape for monitoring the level of airborne particulates which settle on a surface to be sampled, comprising:
   a dimensionally stable, polymeric film backing;
   a pigmented adhesive coating affixed to said polymeric film backing, said adhesive coating having an outer surface; and
   a grid pattern printed on said outer surface of said adhesive coating, said grid pattern including a plurality of orthogonal lines having a color which contrasts with said pigmented adhesive coating.

9. The tape of claim 8 wherein said adhesive coating is fabricated from a pressure sensitive adhesive having an adhesion of not more than about 25 oz./in.

10. The tape of claim 8 further comprising dispensing means for containing the tape, said dispensing means being sealed against external airborne contaminants.

* * * * *